US011026601B2

(12) United States Patent
Granier-Deferre et al.

(10) Patent No.: US 11,026,601 B2
(45) Date of Patent: Jun. 8, 2021

(54) METHOD OF TESTING AN INFANT AND SUITABLE DEVICE FOR IMPLEMENTING THE TEST METHOD

(71) Applicants: Universite Paris Descartes, Paris (FR); Centre National de la Recherche Scientifique (CNRS), Paris (FR); Hester Marie Decasper, Washington, DC (US)

(72) Inventors: Carolyn Granier-Deferre, Paris (FR); Anthony James Decasper, Akron, OH (US); Elodie Hanrion-Monnier, Paris (FR)

(73) Assignees: Universite Paris Descartes; Centre National de la Recherche Scientifique (CNRS)

( * ) Notice: Subject to any disclaimer, the term of this patent is extended or adjusted under 35 U.S.C. 154(b) by 778 days.

(21) Appl. No.: 15/521,075

(22) PCT Filed: Oct. 21, 2015

(86) PCT No.: PCT/EP2015/074377
§ 371 (c)(1),
(2) Date: Apr. 21, 2017

(87) PCT Pub. No.: WO2016/062773
PCT Pub. Date: Apr. 28, 2016

(65) Prior Publication Data
US 2017/0340247 A1    Nov. 30, 2017

(30) Foreign Application Priority Data

Oct. 21, 2014    (FR) ...................................... 1460108

(51) Int. Cl.
*A61B 5/11*    (2006.01)
*A61B 5/00*    (2006.01)
(Continued)

(52) U.S. Cl.
CPC ............ *A61B 5/1124* (2013.01); *A61B 5/162* (2013.01); *A61B 5/168* (2013.01); *A61B 5/742* (2013.01);
(Continued)

(58) Field of Classification Search
CPC ....... A61B 5/1124; A61B 5/742; A61B 5/168; A61B 5/162; A61B 5/7475; A61B 5/6898;
(Continued)

(56) References Cited

U.S. PATENT DOCUMENTS 10,226,171 B2 *   3/2019   Reichow ................ G09B 17/02
10,383,553 B1 *   8/2019   Glenn .................... G16H 10/20
(Continued)

FOREIGN PATENT DOCUMENTS

FR           3027206 A1 *   4/2016   ........... A61B 5/1124

OTHER PUBLICATIONS

Fagan, The Fagan Test of Infant Intelligence Manual (Year: 2005).*
(Continued)

*Primary Examiner* — Jacqueline Cheng
*Assistant Examiner* — Tho Q Tran
(74) *Attorney, Agent, or Firm* — Lerner, David, Littenberg, Krumholz & Mentlik, LLP

(57) ABSTRACT

The invention relates to a method of testing an infant, comprising the following steps: displaying a target on a screen; detecting contact made by the infant with the screen inside and/or outside the target; calculating a success parameter on the basis of the contact detected; and recording the calculated success parameter in a memory.

11 Claims, 8 Drawing Sheets

(51) Int. Cl.
*A61B 5/16* (2006.01)
*A61B 3/024* (2006.01)

(52) U.S. Cl.
CPC ............ *A61B 5/7475* (2013.01); *A61B 3/024* (2013.01); *A61B 5/4082* (2013.01); *A61B 5/6898* (2013.01); *A61B 5/744* (2013.01)

(58) Field of Classification Search
CPC ....... A61B 3/024; A61B 5/744; A61B 5/0482; A61B 5/4082
See application file for complete search history.

(56) References Cited

U.S. PATENT DOCUMENTS

| | | | |
|---|---|---|---|
| 2005/0065452 | A1 | 3/2005 | Thompson |
| 2005/0273017 | A1* | 12/2005 | Gordon .................. A61B 5/048 600/544 |
| 2006/0247153 | A1* | 11/2006 | McMahon ......... A61K 38/1709 514/5.7 |
| 2008/0091512 | A1* | 4/2008 | Marci ...................... A61B 5/16 705/7.29 |
| 2011/0025611 | A1 | 2/2011 | Yoo et al. |
| 2013/0345524 | A1 | 12/2013 | Meyer et al. |
| 2014/0066802 | A1* | 3/2014 | Kaula ...................... A61B 5/16 600/554 |
| 2014/0249447 | A1 | 9/2014 | Sereno et al. |

OTHER PUBLICATIONS

French Search Report for Application No. FR1460108 dated Jul. 14, 2015, 2 pages.

International Search Report for Application No. PCT/EP2015/074377 dated Dec. 18, 2015, 3 pages.

Scerif G et al. "Delineation of early attentional control difficulties in fragile X syndrome: Focus on neurocomputational changes", Neuropsychologia, Pergamon Press, Oxford, GB, vol. 45, No. 8, 1 janvier 2007 (Jan. 1, 2007), pp. 1889-1898, XP026866086.

* cited by examiner

METHOD OF TESTING AN INFANT AND SUITABLE DEVICE FOR IMPLEMENTING THE TEST METHOD

CROSS REFERENCE TO RELATED APPLICATIONS

The present application is a national phase entry under 35 U.S.C. § 371 of International Application No. PCT/EP2015/074377 filed Oct. 21, 2015, published in French, which claims priority from French Patent Application No. 1460108 filed Oct. 21, 2014, all of which are incorporated herein by reference.

FIELD OF THE INVENTION

The invention relates to a method to test a baby and a device adapted to execute the test method.

PRIOR ART

Infants of average prematurity (i.e. born between 32 and 37 weeks Gestational Age (GA)) currently represent 84% of premature births worldwide. Many studies have shown that these infants can present neuro-motor disorders, in particular visuo-manual coordination disorders, sensory (visual and auditive) and cognitive difficulties, including attention and visuo-spatial disorders, learning disabilities, spoken and social communication, and their intellectual efficiency is most often below the norm.

However, these infants generally do not benefit from special monitoring, as is case for substantially premature infants (i.e. born on or before 31 GA). So, in contrast to substantially premature infants with many disorders, the developmental disorders of infants of minor and average prematurity are identified only late in their development, generally towards the age of 3 to 5 years, when starting school, when they are likely to manifest difficulties often unnoticed until then.

It would therefore be necessary to be able to detect developmental disorders in babies, in light of enabling very early care and centred on the specific difficulties of each infant, as is the case for advanced prematurity.

A few classic published tests are available today; they are often revised versions of very old scales for evaluating general, cognitive and social motor development in infants. But the younger the child, the greater the errors in measurement and the lesser the predictive validity of these scales. Aside from the critical problem of the nature of the test items, which are too general and limited to ascertain a precise evaluation of the various elementary cognitive capacities, almost all of these developmental scales are based on the remarks of a practitioner observing the general behaviour of the infant in specific situations, and their success in a series of exercises. Such observation depends on the observer's judgement of the infant's behaviour, and this judgement rests substantially on the extent of his experience, constituting a source of additional error. Therefore, these scales must be used only by highly experienced practitioners with specific training. These two factors contribute considerably to the very low coefficients of test-retest fidelity ($r \leq 0.40$), id est the considerable variability of scores attributed to the same infant at the same age, the low concordance of scores attributed by different evaluators to infants under 2 years, and therefore, at their very low predictive power concerning the cognitive and social sphere, or even the overall motor development of the infant or their visuo-manual coordination and fine movements.

Tests used to evaluate babies from 0 to 6 months concentrate essentially on evaluating reflexes, orientation and the fields of perception and motor skills, and/or the emergence of communication in general. There are few tests concentrating on the cognitive sphere, and in particular on the capacities for learning and representation, since research on the intelligence of babies who are a few months old is relatively recent and ongoing. The Fagan test is a rare example of such an assessment ("The Fagan Test of intelligence: A technical summary", Journal of Applied Developmental Psychology, Joseph F. Fagan III, Douglas K. Detterman, Volume 13, Issue 2, April-June 1992, pages 173-193). It represents considerable progress in cognitive evaluation of the baby. However, it relies solely on the infant's reaction to something new, measured by how long they stare, and is therefore limited to evaluating recognition memory. This is why its predictive validity, as relates to the cognitive sphere, and although superior to that of other tests, is nevertheless considered highly inadequate for estimating developmental delays or predicting the IQ of at-risk infants later in life.

SUMMARY OF THE INVENTION

An aim of the invention is to provide a solution for testing babies more precisely and more reliably than with conventional tests based on observation.

This problem is resolved in terms of the present invention by a method to test a baby comprising steps of:
displaying a target on a screen,
detecting contact made by the baby on the screen inside and/or outside the target,
calculating a success parameter as a function of the contacts detected, and
recording the calculated success parameter in a memory.

The proposed method makes it possible to detect contact made by the baby with the screen, including very short instances ($\leq 10$ milliseconds)

The data obtained is consequently more precise and more reliable than that obtained from classic observational tests, because the success parameter is objective and does not depend on human judgement. This means they can easily be compared with reference parameters.

Also, the proposed method can be executed by many professionals, and does not require specific or lengthy prior training.

The calculated success parameter can comprise, for example, a distance between a point of contact between the baby and the screen and a position of the target displayed on the screen.

The calculated success parameter can also include the duration between two successive contacts between the baby and the screen inside and/or outside the target.

The calculated success parameter can comprise a success rate equal to the ratio between a number of contacts inside the target and a number of contacts outside the target.

The calculated success parameter can comprise a success rate equal to the ratio between a number of contacts inside the target and a total duration of the test.

According to a first embodiment of the method, an active target and an inactive target are displayed on the screen, and the method comprises a step of:
when contact between the baby and the screen inside the active target is detected, it triggers or modifies visual and/or aural stimulation.

According to a second embodiment of the method, a first active target and a second active target are displayed on the screen, and the method comprises steps of:

when contact between the baby and the screen inside the first active target is detected, it triggers a visual and/or aural stimulation, and when contact between the baby and the screen inside the second active target is detected, it triggers a visual and/or aural stimulation, different to the first visual and/or aural stimulation.

According to a third embodiment of the method, the method comprises a step of:

when contact between the baby and the screen inside the target is detected, it shifts the target on the screen from one position to a following position according to a predetermined sequence of positions.

The shifting from one position to the other can be associated with a sound sequence successively or simultaneously.

The predetermined sequence of positions can comprise a start position, and the method comprises a step of:

displaying the target in the start position if after preceding contact inside the target no other contact is detected during a predetermined duration.

In one of the positions of the sequence, display of the target can be omitted.

The method can also comprise a step of:

displaying a mask in a zone of the screen, and in one of the positions of the sequence, the target is hidden by the mask.

The mask can be displayed before or after the target is displayed in the position of the sequence in which the target is hidden by the mask.

The target preferably represents a face or other visual form attractive to the baby.

The target preferably measures between 0.5 and 5 centimetres in length.

Also, the method can also comprise a step of:

displaying the calculated success parameter on the screen.

The invention also relates to a test device of a baby comprising a touch screen and a processing module configured to execute the steps of the method such as defined previously.

The test device can be in the form of a tablet integrating the touch screen and the processing module in a single device.

In use, the test device is preferably placed on a table at an inclination relative to the table of between 40 and 50°, preferably 45°. This inclination lets the infant easily reach the screen of the device, with motor coordination capacities associated with their age.

The invention also relates to a computer program product comprising code instructions for execution of a method such as defined previously.

The invention also relates to a storage medium readable by computer equipment on which a computer program is recorded comprising code instructions for executing a method such as defined previously.

PRESENTATION OF DIAGRAMS

Other characteristics and advantages will emerge from the following description that is purely illustrative and non-limiting and must be considered with respect to the attached figures, in which:

FIG. 1 schematically illustrates a device for testing a baby according to an embodiment of the invention, FIG. 2 is a diagram schematically illustrating steps of the first phase of a test method according to an embodiment of the invention, FIG. 3 schematically illustrates a screen of the device during the first phase of the method, FIG. 4 is a diagram schematically illustrating steps of a second phase of the test method, FIG. 5 schematically illustrates a screen of the device during the second phase of the method, FIG. 6 schematically illustrates a target that can be used during the different phases of the method, FIG. 7 is a diagram schematically illustrating steps of a third phase of the test method, FIG. 8 schematically illustrates a screen of the device during the third phase of the method, FIGS. 9, 10, 11A and 11B schematically illustrate results, which can be obtained via the test method.

DETAILED DESCRIPTION OF AN EMBODIMENT

In FIG. 1 the test device 10 illustrated generally comprises a processing module 11, a data storage module 12 and a display module 13.

The processing module 11 is a processor configured to execute the steps of the test method. Alternatively, the processing module 11 can be an electronic card, dedicated integrated circuit or programmable electronic component.

The storage module 12 is a memory in which a program comprising code instructions for executing the test method by the processing module 11 is recorded. The memory 12 is also conducive to containing the measurement data recorded during running of the program. The memory can be a hard disc ("Hard Disk Drive"), a memory EEPROM ("Electrically-erasable programmable read-only memory") or a flash memory (for example of "Solid State Drive" type) in fixed or removable form (for example in the form of a USB connector key).

The display module 13 comprises a touch screen 14. The touch screen 14 is on the one hand conducive to being controlled by the processing module 11 for displaying test pages and on the other hand detecting coordinates of a point of contact between a user and the touch screen 14.

The test device 10 can also comprise a loudspeaker 15.

The test device 10 can be in the form of a tablet integrating the processing module 11, the storage module 12, the display module 13 and the loudspeaker 15 in a single device.

The program can be present initially in the memory 12 of the device 10 or be downloaded by the user then recorded in the memory 12 of the device 10.

The test method as conducted comprises three successive phases.

The first phase 100 of the test method (illustrated in FIGS. 2 and 3) corresponds to simple associative learning by contacts on fixed tactile zones.

Aside from attention capacities and work memory, this first phase aims to evaluate either the comprehension of the contingency between some movements of the infant and a sensory "return" (reinforcement) specific to the environment, or comprehension of the contingency (synchrony) between two different sensory stimulations, which can be simultaneous or successive. This first phase can also evaluate capacities for recognizing novelty, capacities for discriminating some elements between aural stimulations or between visual stimulations, and therefore the perceptive finesse and recognition memory of the infant.

The second phase 200 of the test method (illustrated in FIGS. 4 to 6) consists of testing if the baby can successively touch a target moving along a predetermined trajectory.

This second phase allows more extended observation of the attention, of the working memory and representation capacities of the baby, those of a dynamic object and a trajectory, therefore a spatio-temporal representation more complex than that of the preceding phase, during a task of a level of disability above the plane of visuo-manual coordination.

The third phase 300 of the test method (illustrated in FIGS. 7 and 8) is performed in the continuity of the second phase.

This third phase evaluates the capacity for anticipation in time and space of shifts of the target and/or the capacity to represent the presence of a hidden object (permanence of the object), and therefore the memory capacities of visuo-spatial work of the infant.

The test method progresses as follows.

The observer in charge of supervising running the method places the baby to be tested in front of the screen 14.

In terms of the present application "baby" means an infant aged from 0 to 6 months. In the case of an infant born prematurely, it is the corrected age of the infant that is taken into account.

In a first instance, the baby is placed in a front child carrier, slightly rigid, worn by a parent or next of kin well known to the infant, with which the infant is given time to become familiarised.

The observer controls the start of the program in the device 10. The observer can launch the start of the program by selecting an appropriate icon corresponding to this program in a menu of the device.

In a second instance, the parent or next of kin is seated comfortably on an adjustable chair, at a sufficient distance for the infant to manually reach all the zones of the screen 14 dedicated to the method in use, the eyes of the baby preferably being at a distance of around 15 to 30 centimetres from the screen 14.

The room in which the baby is tested must be empty, apart from those elements necessary for the test, preferably be of a light and even colour, without any disrupting visual or sound element, which might attract the attention of the infant. The room is also in relative semi-darkness to maximise the attention of the infant and for maximum focus of their attention on the screen 14.

First Phase of the "Choice Test" Method:

FIG. 2 is a diagram schematically illustrating the steps of the first phase 100 of the test method.

According to a first step 101, the processing module 11 controls the display module 13 for displaying a first test page on the screen 14.

The first test page 16 is illustrated in FIG. 3. The first test page 16 contains a first target 17 (called "active target") and a second target 18 (called "inactive target"). In the example illustrated in FIG. 3, each target 17, 18 comprises a coloured zone of the page. Each zone 17, 18 can have a rectangular form. The zones 17 and 18 are located side by side at the bottom of the screen 14.

According to a second step 102, the display module 13 detects the contact or contacts of the baby with the screen 14. More precisely, the display module 13 detects the coordinates (abscissa and ordinate) of the points of contact of the baby with the screen 14. The display module 13 transmits the detected coordinates to the processing module 11.

Each contact of the baby with the screen 14 initiates the following steps.

According to a third step 103, the processing module 11 determines if the point of contact is located in the active target 17.

If this is the case, according to a fourth step 104, the processing module 11 controls emission by the device 10 of a stimulation comprising a sound and/or visual signal.

The signal sound can for example consist of a spoken or musical sequence, different languages or different tonalities, for example a message of encouragement, sent by the loudspeaker 15, according to the activated target.

The visual signal can for example comprise the temporary display of an icon 19, a drawing or a video on the screen 14.

If the point of contact is located outside the active target 17, the processing module 11 does not control emission of a stimulation.

At the same time, according to a fifth step 105, for each contact detected, the processing module 11 controls the recording in the storage module 12 of coordinates of points of contact and instants of contact (time elapsed since the start of the test, in milliseconds). The coordinates of points of contact and the instants of contact are recorded in chronological order of contacts.

Each couple of contact coordinates is associated in the storage module 12 with an instant of contact, and a numeral representative of the order of appearance of the contact.

At the end of a test period determined by the behaviour of the infant and their attention to the task, the processing module completes the test and executes a sixth step.

According to the sixth step 106, the processing module 11 calculates one or more success parameters as a function of all data recorded in the storage module 12 during step 105.

The success parameters calculated can be the following:
a total duration of the first test phase,
for each target 17, 18, the total number of contacts on the target during the total period of the first test phase,
for each target 17, 18, the duration between two successive contacts of the baby with the screen 14 inside and/or outside the target,
a success rate equal to the ratio between a number of contacts inside the active target 17 and a number of contacts outside the active target 17.

The processing module 11 can also calculate the following parameters:
for each target 17, 18, the ratio between the total number of contacts on the target and the total duration of the first test phase,
for each target 17, 18, the average frequency of contacts (in number of contacts per unit of time), in their chronological order.
for each target 17, 18, the average and total duration of contacts,
a variation of the ratio of the number of contacts inside the active target 17 to the number of contacts on the inactive target 18, over the time during the period of the first test phase (this variation is called "learning curve").

According to a seventh step 107, the processing module records the parameters calculated in the storage module.

According to an eighth step 108, the processing module 11 can control display, on the screen 14, of parameters calculated during the first phase 100 of the test method. The observer can view the results of this first phase.

In a variant of this first phase of the method, the two targets 17 and 18 can be active targets.

In this case, the fourth step is modified such that:
when contact between the baby and the screen inside the first active target 17 is detected, the processing module 11 controls emission of a first stimulation comprising a first visual and/or sound signal, and when contact of the baby with the screen inside the second active target 18 is detected, the processing module 11 controls emission of a second stimulation comprising a second visual and/or sound signal, different to the first visual and/or sound signal.

Second Phase of the Method: "Contact and Tracking of a Moving Target"

This second phase can be performed if the observer considers that the motor coordination capacities of the infant have proven sufficient during the first phase.

FIG. 4 is a diagram schematically showing steps of the second phase 200 of the test method.

According to a first step 201, the processing module 11 controls the display module 13 for displaying a second test page 20 on the screen 14.

The second test page 20 is shown in FIG. 5. The second test page 20 contains a target 21. In the example illustrated in FIG. 5, the target 21 schematically illustrates a face. The target 21 is positioned at the bottom of the screen 14 in a start position P1.

FIG. 6 illustrates in more detail the form of the target 21. The target 21 is designed specially to attract the attention of babies. The target 21 presents for example a circular form and a lively colour yellow, for example). It comprises two smaller circles 22 representing eyes and an arced line 23 representing a smiling mouth. The dimensions of the target 21 are particularly adapted to the dimensions of the hands of the babies. The target 21 has a diameter D of between 3 and 5 centimetres, preferably of the order of 4 centimetres. In the event where the screen 14 comprises pixels whereof the size is 0.27 millimetres×0.27 millimetres, the diameter of the target 21 is around 148 pixels and the area of the target is of the order of 17200 pixels.

The position of the target 21 on the screen 14 is defined by the horizontal (abscissa along the axis X) and vertical (ordinate along the axis Y) coordinates of the centre O of the target.

According to a second step 202, the display module detects the contact or contacts of the baby with the screen. More precisely, the display module 13 detects the coordinates (abscissa and ordinate) of the points of contact of the baby with the screen 14 and sends the detected coordinates to the processing module 11.

Each contact of the baby with the screen 14 triggers the following steps.

According to a third step 203, the processing module 11 determines if the point of contact is in the target 21.

If this is the case, according to a fourth step 204 the processing module 11 controls the shifting of the target 21 on the screen 14 from a position Pi to a following position Pi+1, according to a predetermined sequence of positions.

The shifting can be accompanied by emission of a stimulation sound, for example a message of encouragement.

The target 21 is therefore shifted from a position Pi to a following position Pi+1 according to the predetermined sequence. The sequence comprises a number N of successive predetermined positions, going from a start position P1 to an arrival position PN according to a predetermined trajectory. The number N can be equal to 3 for example.

When the target 21 is in the arrival position PN of the sequence, the processing module 11 controls the shifting of the target 21 on the screen 14 from the arrival position PN of the sequence to the start position P1 of the sequence (reinitialisation of the sequence).

If the point of contact is outside the target 21, the processing module 11 does not control the shifting of the target 21. The target 21 is kept in its current position.

Also, no aural stimulation is emitted.

However, if no contact is detected in the target 21 over a period greater than a maximal predetermined duration display, the processing module 11 controls the shifting of the target 21 in the start position P1 (reinitialisation of the sequence).

In other words, the shifting sequence is reinitialised so as to reengage the attention of the baby.

The maximal duration of display can be between 5 and 20 seconds and is preferably of the order of 10 seconds.

At the same time, according to a fifth step 205 at each contact detected the processing module 11 controls recording in the storage module 12 of coordinates of the points of contact and instants of contact. Each couple of contact coordinates is associated in the storage module 12 with an instant of contact.

On completion of a test period determined by the behaviour and attention of the infant on the task, the processing module 11 completes the test and executes a sixth step.

According to the sixth step 206, the processing module 11 calculates one or more success parameters as a function of all data recorded in the storage module 12.

The success calculated parameters can be the following:
distance between each point of contact and the centre O of the target 21,
duration between two successive contacts made by the baby with the screen 14 inside and/or outside the target 21,
success rate equal to the ratio between a number of contacts inside the target 21 and a number of contacts outside the target 21.

The processing module 11 can also calculate the following parameters:
a total duration of the second test phase,
a total number of contacts on the screen 14 during the total period of the second test phase,
an average frequency of contacts (in number of contacts per unit of time),
a total number of contacts on the target 21 during the total period of the second test phase,
an average frequency of contacts on the target 21 (in number of contacts per unit of time),
an average frequency of contacts on the target 21 over the whole test (in number of contacts/total duration of the test phase),
a total number of contacts outside the target 21 during the total period of the second test phase,
an average frequency of contacts outside the target 21 (in number of contacts per unit of time),
an average frequency of contacts outside the target 21 over the whole test (in number of contacts/total duration of the test phase),
a total number of series of two successive contacts on the target 21,
a frequency of series of two successive contacts on the target 21 (in number of series per unit of time),
a total number of series of N successive contacts on the target 21, N being a whole number greater than or equal to 3,
a frequency of series of N successive contacts on the target 21 (in number of series per unit of time),
a total number of series of successive contacts on the target 21,
a frequency of series of successive contacts on the target 21 (in number of series per unit of time), a variation in the time elapsed between two successive contacts on the target 21 (that is, between a contact on the target 21 and a following contact on the target 21 once the target 21 has moved), over time, during the period of the second test phase (this variation is called "learning curve"), a number of sequences of shifting of the target made during the total period of the second test phase, a time total elapsed during the second test phase, without contact on the target 21.

According to a seventh step 207, the processing module 11 records the calculated parameters in the storage module 12.

According to an eighth step 208, the processing module 11 can control display, on the screen 14, of parameters calculated during the second phase 200 of the test method. The observer can view the result of the second phase of the method.

Third Phase of the Method: "Contact, Tracking and Motor Anticipation of a Shifting Target"

The third phase is initiated only if the infant was capable of making several successive series of contacts on the target in movement during the second phase. In other words, the third phase of the test method illustrates a suite possible of the second phase of the test method.

FIG. 7 is a diagram schematically representing steps of the third phase 300 of the test method.

Steps 301 to 308 of this third phase of the method are identical to steps 201 to 208 of the second phase of the method.

The third phase 300 of the method however comprises an additional step 309, according to which the processing module 11 controls the display module 13 for displaying a mask 24 on the screen 14. The mask 24 comprises a coloured zone of the screen 14. The zone can have a rectangular form.

As illustrated in FIG. 8, the third test page 25 displayed is identical to the second test page 20, except that the third test page 25 contains the mask 24.

The mask 24 extends over one or more positions Pj to Pk of the sequence, such that it conceals the target 21 when the target 21 is in each of positions Pj to Pk.

In this way, the target 21 is shifted from a position Pi to a following position Pi+1, according to the same predetermined sequence of positions as during the second phase of the method. However, in this third phase some positions Pj to Pk of the target 21 cannot be seen by the baby due to the mask 24.

Alternatively, in place of using a mask 24, the display of the target 21 can be omitted in the positions Pj to Pk.

According to the sixth step 306, the processing module 11 calculates one or more success parameters as a function of all data recorded in the storage module 12. The same parameters are calculated as during step 206.

However, the calculated success parameters also comprise the following parameters:

number of contacts on the target 21 when the target is masked or omitted, frequency average of contacts in the target 21 when the target is masked or omitted (in number of contacts per unit of time).

According to the seventh step 307, the processing module 11 records the calculated parameters in the storage module 12.

According to the eighth step 308, the processing module can control display on the screen 14 of parameters calculated during the third phase 300 of the test method. The experimenter can view the result of the third phase of the method Implementation Example Forty-eight babies aged on average 4 months and 2 days (412 days GA) were tested with the test method, including:

group 1: 30 full-term babies (14 girls and 16 boys), average age 126 days (average GA 412 days±9 days).

group 2: 12 premature babies (6 girls and 6 boys), average GA 418 days±12 days, group 3: 6 "at risk" babies (average age 122 days±9 days), presenting plagiocephaly and/or intra-uterine growth retardation (RCIU) or a strabismus, 4 full-term and 2 premature babies (3 girls and 3 boys).

FIGS. 9 and 10 present the results obtained with each group of infants.

Figure 1:
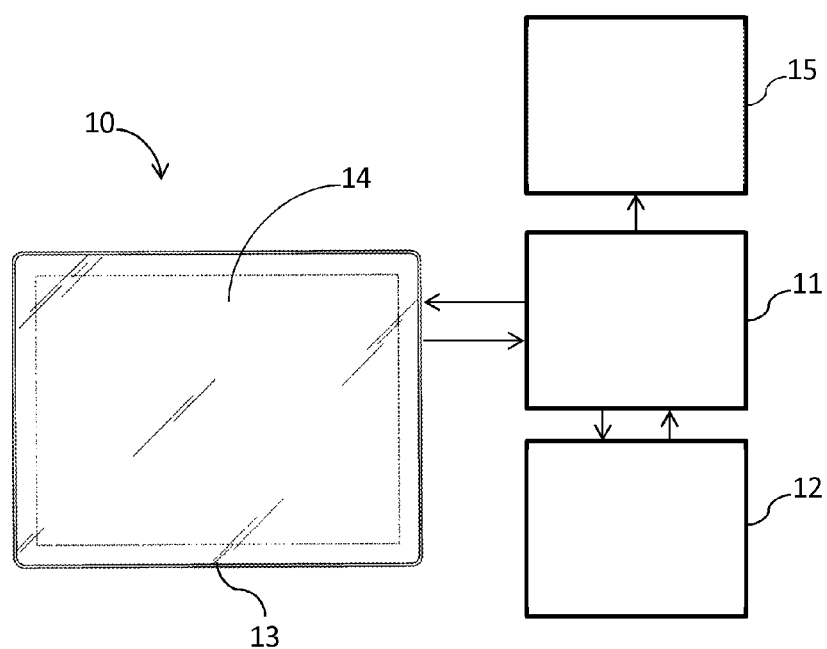
Figure 2:
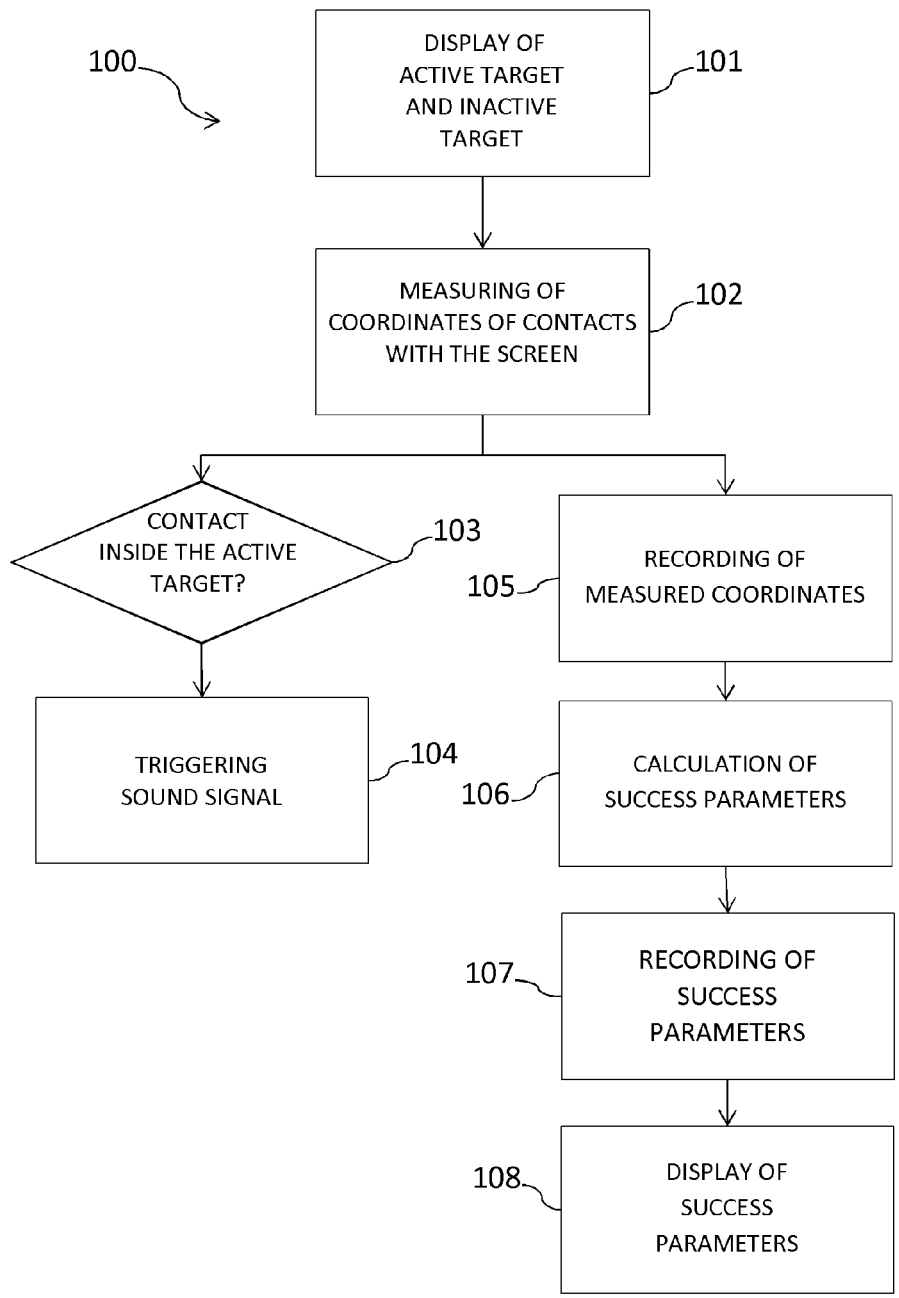
Figure 3:
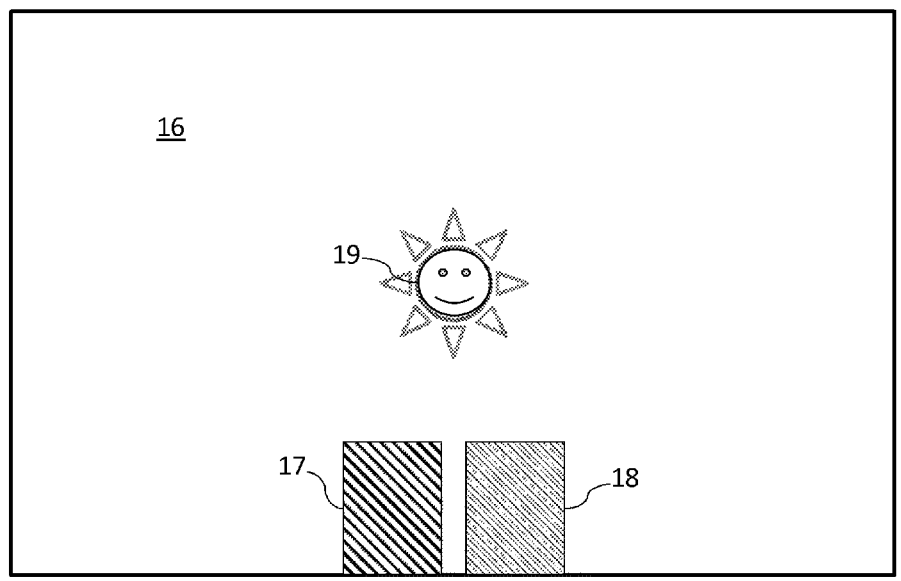
Figure 4:
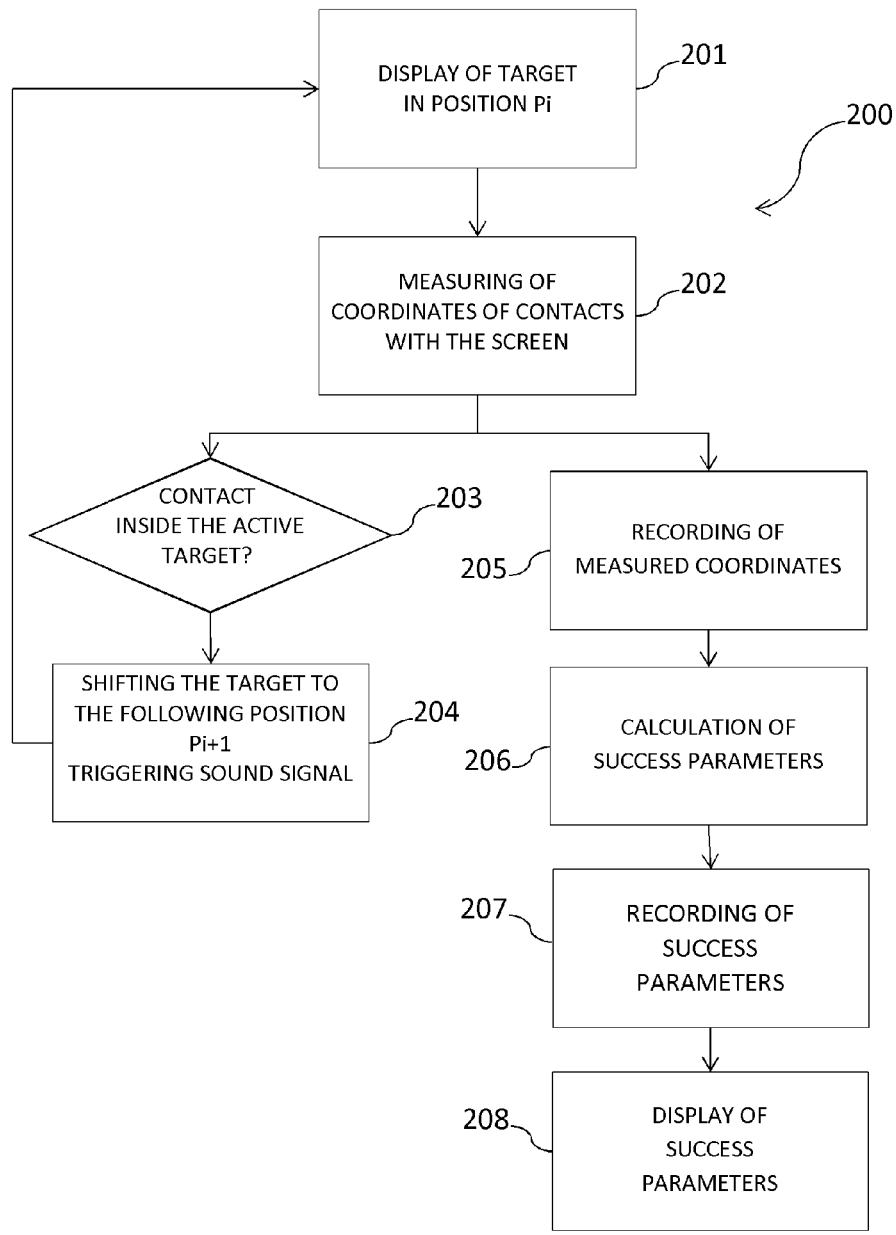
Figure 5:
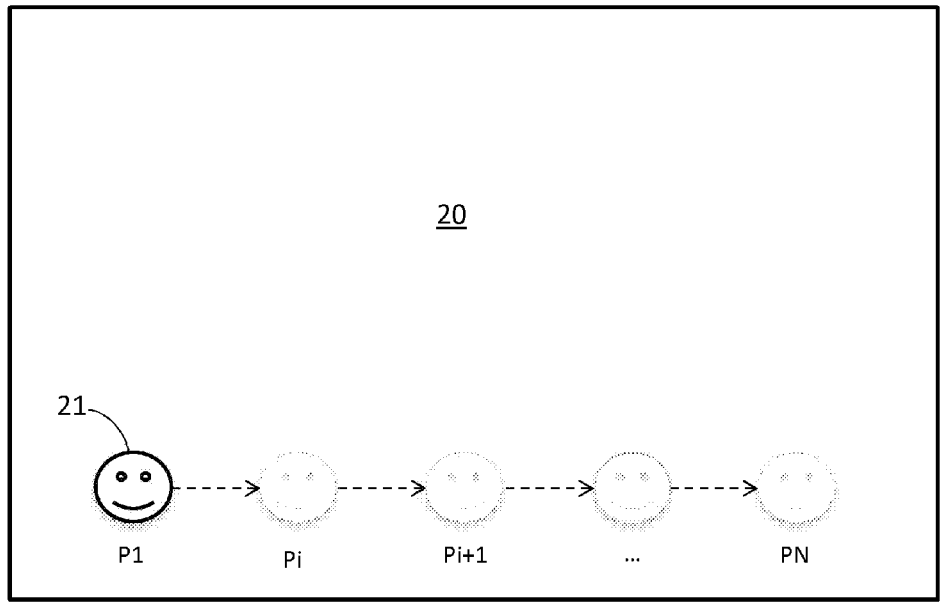
Figure 6:
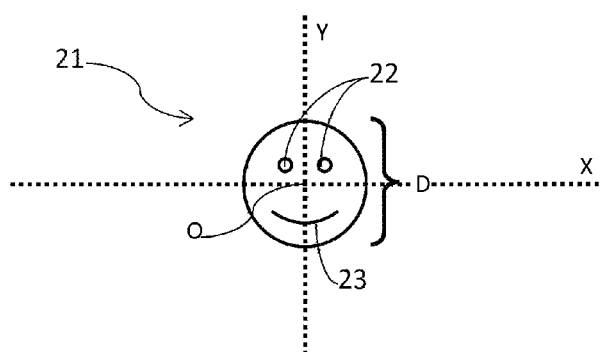
Figure 7:
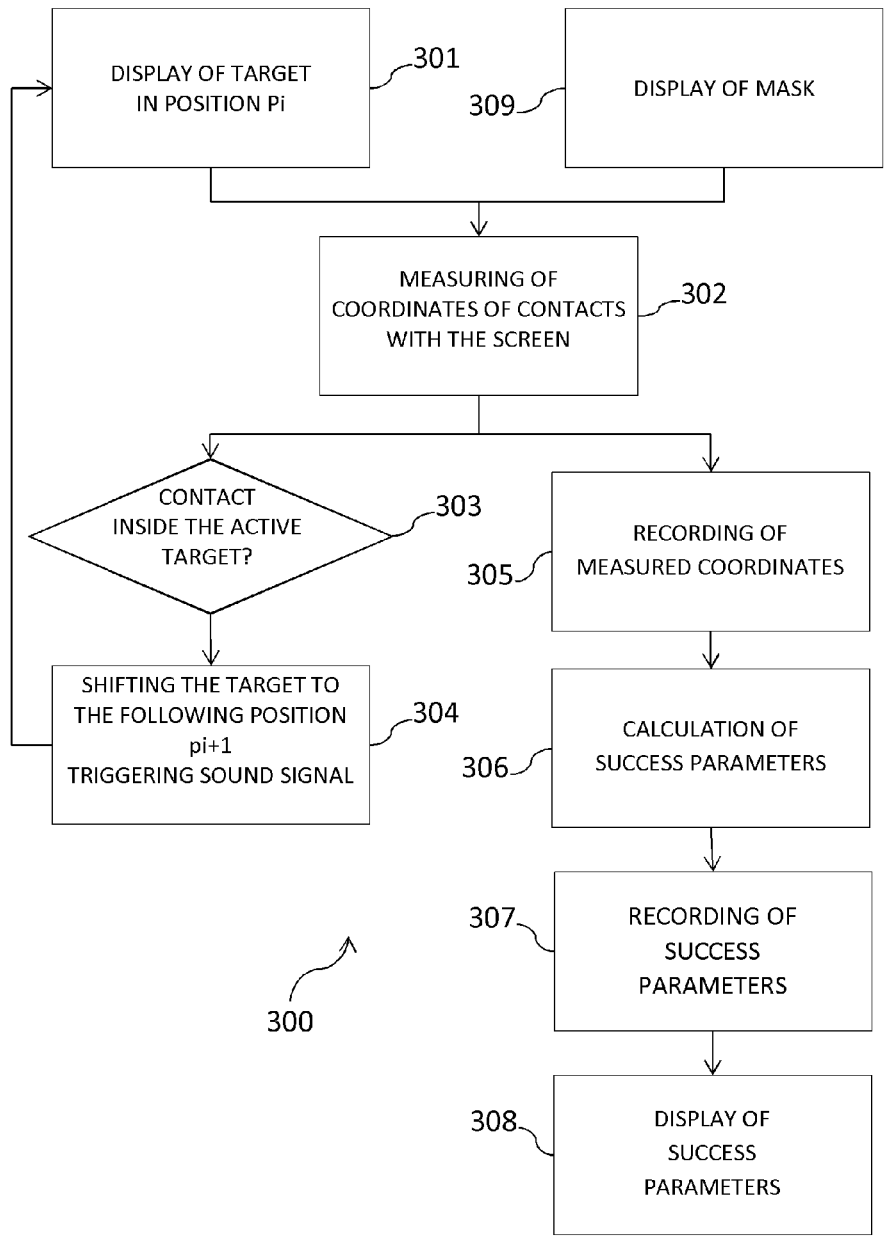
Figure 8:
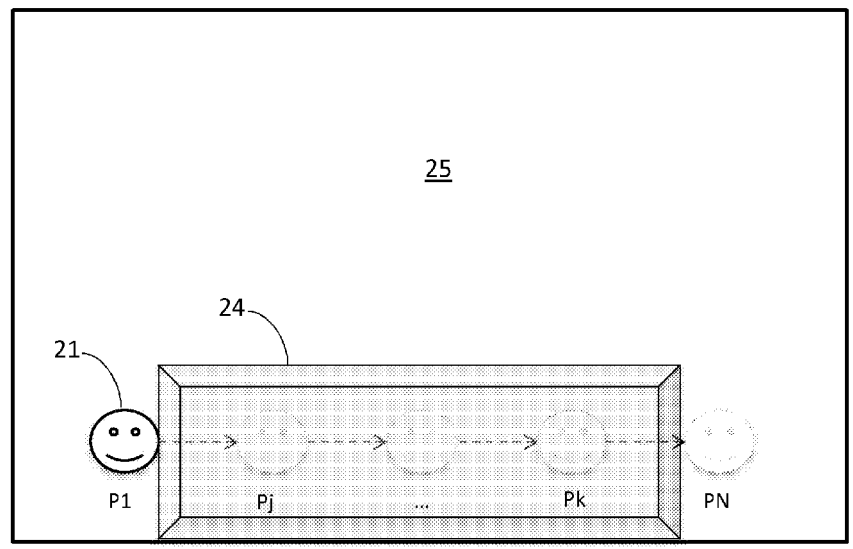
Figure 9:
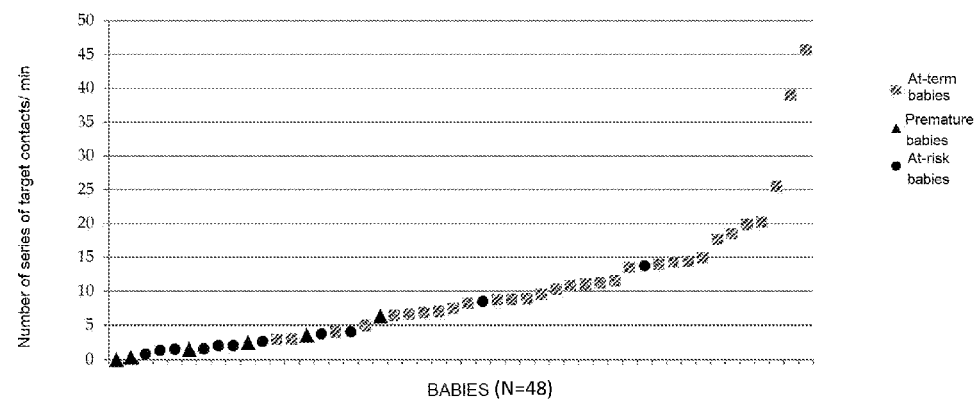
FIG. 9 is a diagram representing the average frequency of contacts (in number of contacts per minute) for each infant tested.
Figure 10:
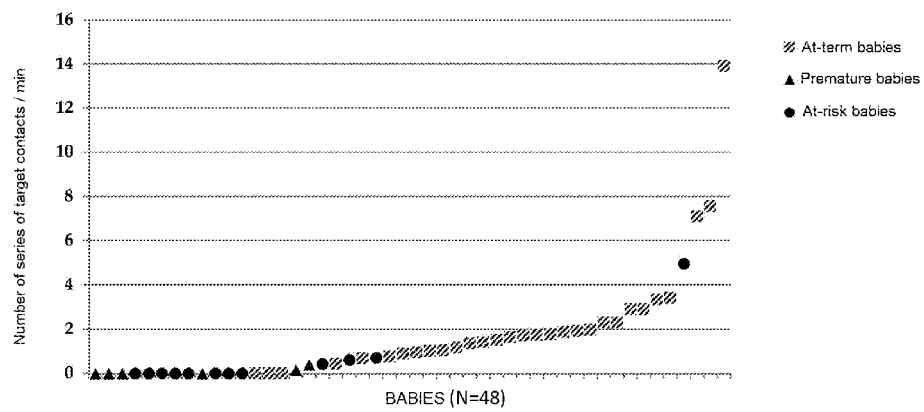
FIG. 10 is a diagram representing the frequency of series of contacts (in number of series of contacts per minute) for each baby tested.

It is clear that in comparison with full-term babies, premature babies generate on average almost 4 times fewer contacts on the target per min (3.72 vs. 13.36; $U=32$; $p<0.0001$, where U is the Mann Whitney statistic and p indicates a probability that the result is due randomly), and 4 times fewer series of contacts on the target per minute than full-term babies (0.56 vs. 2.31; $U=51$; $p<0.0001$); this difference is also statistically significant for the series of 2 ($U=61$; $P=0.001$) and the series of 3 contacts ($U=115$; $P=0.04$). But the average duration of visual attention (181 sec vs. 130 sec) and the average number of contacts on the screen per min. (36 vs. 50) do not differ significantly between full-term and premature babies.

If those at-risk babies presenting pathology at birth are considered, relative to the full-term babies they generate almost 6 times fewer contacts on the target per min (2.36 vs. 13.36; $U=4$; $p<001$), and 25 times fewer series of contacts on the target per minute (0.09 vs. 2.31; $U=12$; $p=0.001$).

In fact, a single baby has made a series of contacts.

Also, the average adjustment of the contact on the target is 1.5 times lower relative to that of full-term infants (281 px. vs. 184 px; $U=19$; $p=0.003$).

These at-risk babies do not differ on average from premature babies, except on the average adjustment of the contact ($U=4$; $P=0.003$), which is 1.6 times lower (281 px. vs. 177 px).

Figure 11A:
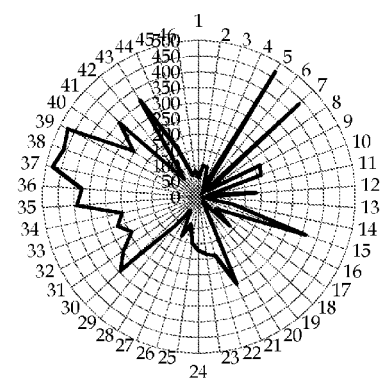
Figure 11B:
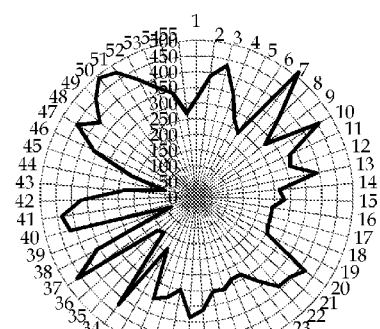

FIGS. 11A and 11B schematically illustrate results such that they can be displayed on the screen 14 on completion of the second phase of the method. These figures chronologically illustrate (clockwise), the distance (in number of pixels) between the point of contact and the centre of the target in movement during the second phase of the method, respectively for a full-term and for a premature baby.

It is evident that the total number of contacts generated by the premature baby is substantially identical to the number of contacts generated by the full-term baby. But the premature baby generates no contact inside the target (in this case, the target does not move) whereas the full-term baby born is capable of making a series of 2 to 3 successive contacts with the target.

This example shows that the proposed test method is adapted particularly to the level of development of babies aged from 3 to 5 months without pathology, and that these babies present statistically significantly performances clearly superior to those of babies born prematurely or who are "at risk."

The proposed method effectively discriminates the different groups of infants. Also, the considerable inter-individual variability of results observed inside the group of full-term infants, as well as inside the group of premature infants, indicates that the discriminative finesse of the method is very satisfactory, while it also differentiates between them the infants of the group, a prerequisite to any valid evaluation.

Such results, very precise and reliable, could not have been obtained from classic developmental ranges. Also, comparison of data obtained with the three test phases could estimate the origin of difficulties of the infant, in particular if these difficulties essentially come from disorders or retardation of motor coordination, attention deficits, or sensory or perceptive disorders, or even for example the disability to learn by rule, such as identifying stable contingencies/associations, between the behaviour of the infant and the initiated stimulations, or again between simultaneous or successive sensory stimulations. The program in fact comprises several test modules corresponding to different possible test phases; these can vary as a function of the characteristics of targets, and of those of the visual and auditive sequences. The infant can be retested another day by focusing on specific elementary capacities to better understand the origin of their disorders. The proposed test method can be applied not only to detect developmental disorders in babies, but also for measuring the evolution of their disorders once treatment adapted to the infant's specific needs has been implemented.

The invention claimed is:

1. A method to test an infant aged from 0 to 6 months comprising a test phase (200, 300) comprising steps of:
    displaying a target (17, 18, 21) on a computer screen (14),
        detecting points of contact and instants of contact of the infant with the computer screen (14) inside and/or outside the target (17, 18, 21) using a processing module (11), wherein the points of contact and the instants of contact are recorded in a chronological order,
    after a contact between the infant and the computer screen (14) inside the target (21) is detected, shifting the target (21) on the computer screen from a position (Pi) to a following position (Pi+1) according to a predetermined sequence of positions,
    calculating, using the processing module (11), a success parameter as a function of the points of contact and/or the instants of contact detected, and
    recording the calculated success parameter in a computer memory (12),
    wherein the calculated success parameter comprises at least one of:
        a distance between a point of contact of the infant with the computer screen (14) and a position of the target (17, 18, 21) displayed on the computer screen (14);
        a duration between two successive instants of contact of the infant with the computer screen (14) inside and/or outside the target (17, 18, 21);
        a success rate equal to the ratio between a number of contacts inside the target (17, 18, 21) and a number of contacts outside the target (17, 18, 21); and
        a success rate equal to the ratio between a number of contacts inside the target (17, 18, 21) and a total duration of the test.

2. The method as claimed in claim 1, wherein the predetermined sequence of positions comprises a start position (P1), the method comprising a step of:
    if no contact is detected during a predetermined duration, displaying the target (21) in the start position (P1).

3. The method as claimed in claim 1, wherein, in one of the predetermined sequence of positions (Pj-Pk) of the sequence, the display of the target (21) is omitted.

4. The method as claimed in claim 1, comprising a step of:
    displaying a mask (24) in a zone of the computer screen (14),
    wherein, in one of the positions (Pj-Pk) of the sequence, the target (21) is hidden by the mask (24).

5. The method as claimed in claim 4, wherein the mask (24) is displayed before or after the target (21) is displayed in the position (Pj-Pk) of the sequence in which the target (21) is hidden by the mask (24).

6. The method as claimed in claim 1, wherein the target (21) has a dimension between 0.5 and 5 centimetres.

7. The method as claimed in claim 1, comprising a step of:
    displaying the calculated success parameter on the computer screen (14).

8. The method as claimed in claim 1, comprising another test phase (100) during which an active target (17) and an inactive target (18) are displayed on the computer screen (14), the other test phase (100) comprising a step of:
    after a contact between the infant and the computer screen (14) inside the active target (17) is detected, triggering visual and/or aural stimulation.

9. The method as claimed in claim 1, comprising another test phase (100) during which a first active target (17) and a second active target (18) are displayed on the computer screen (14), the other test phase (100) comprising steps of:
    after a contact between the infant and the computer screen (14) inside the first active target (17) is detected, triggering a first visual and/or aural stimulation, and
    after a contact between the infant and the computer screen (14) inside the second active target (18) is detected, triggering a second visual and/or aural stimulation, different to the first visual and/or aural stimulation.

10. A test device (10) of an infant comprising a touch screen (14) and a processing module (11) configured to execute the steps of the method as claimed in claim 1.

11. A non-transitory storage medium readable by computer equipment on which a computer program is recorded, comprising code instructions for execution of a method as claimed in claim 1.

* * * * *